United States Patent [19]
Touzuka et al.

[11] 4,057,584
[45] Nov. 8, 1977

[54] PROCESS FOR PREPARING HEXAFLUOROPROPANONE-2

[75] Inventors: Takashi Touzuka, Settsu; Yonosuke Ohsaka, Takatsuki, both of Japan

[73] Assignee: Daikin Kogyo Co., Ltd., Osaka, Japan

[21] Appl. No.: 695,110

[22] Filed: June 11, 1976

[30] Foreign Application Priority Data

June 24, 1975 Japan .................................. 50-79021

[51] Int. Cl.$^2$ ............................................. C07C 45/04
[52] U.S. Cl. ............................. 260/593 H; 252/442; 260/653.3; 260/653; 260/544 F; 260/348.48; 260/348.32
[58] Field of Search ........... 260/593 H, 597 R, 544 Y, 260/544 F, 348 R

[56] References Cited
U.S. PATENT DOCUMENTS

| 2,712,554 | 6/1955 | Miller | 260/593 H |
| 3,321,515 | 5/1967 | Moore et al. | 260/593 H |
| 3,959,367 | 5/1976 | Jeffrey | 260/348.5 V |

FOREIGN PATENT DOCUMENTS

| 2,424,852 | 5/1974 | Germany | 260/593 H |

OTHER PUBLICATIONS

Gerberich et al, J. Catalysis, vol. 6, pp. 209–219 (1966).

*Primary Examiner*—James O. Thomas, Jr.
*Assistant Examiner*—James H. Reamer
*Attorney, Agent, or Firm*—Stevens, Davis, Miller & Mosher

[57] ABSTRACT

A process for preparing hexafluoropropanone-2 from hexafluoropropene by one step reaction which comprises contacting hexafluoropropene and oxygen with a fluorinated alumina as a catalyst.

2 Claims, No Drawings

PROCESS FOR PREPARING HEXAFLUOROPROPANONE-2

The present invention relates to a process for preparing hexafluoropropanone-2. More particularly, it relates to a process for preparing hexafluoropropanone-2 from hexafluoropropene with a high efficiency by the use of a specific catalyst.

Hexafluoropropanone-2 is useful by itself as a catalyst for polymerization of perfluorocyclobutene or triazine. Because of its polymerizability, it forms a terpolymer with tetrafluoroethylene and ethylene. It is also useful as the starting material for the production of bisphenol AF (($C_6H_4$—OH)$_2$C(CF$_3$)$_2$) which is an excellent cross-linking agent for fluorine-containing elastomers.

For production of hexafluoropropanone-2, there is known a method which comprises oxidizing hexafluoropropene and subjecting the resultant 1,2-epoxyhexafluoropropane to rearrangement to obtain hexafluoropropanone-2. For example, hexafluoropropene and oxygen are contacted with activated silica gel at a temperature of 140° to 280° C to obtain 1,2-epoxyhexafluoropropane, which is then subjected to rearrangement in the presence of a Lewis acid such as aluminum oxide to give hexafluoropropanone-2 (U.S. Pat. No. 3,775,439). Thus, in the conventional method, two steps of reaction are required for the production of hexafluoropropanone-2.

As the result of extensive studies, it has now been found that hexafluoropropanone-2 can be prepared from hexafluoropropene and oxygen by one step of reaction when a specific catalyst, i.e. fluorinated alumina, is used. The present invention is based on this finding.

According to the present invention, there is provided a process for preparing hexafluoropropanone-2 from hexafluropropene by one step which comprises contacting hexafluoropropene and oxygen with a fluorinated alumina as a catalyst to give hexafluoropropanone-2.

The catalyst to be used in the process of the present invention is fluorinated aluminas, of which some are known as catalysts in reforming of hydrocarbons and some others are known as catalysts in rearrangement of chlorofluorohydrocarbons. While any catalyst known as fluorinated alumina can be used in the process of this invention, such fluorinated alumina comprises essentially aluminum, fluorine and oxygen and its fluorine content is desired to be from about 0.5 to 50% by weight.

The fluorinated alumina as the catalyst is ordinarily prepared by treatment of activated alumina with a fluorinating agent.

As the activated alumina, there can be employed, without particular limitation, any conventional one such as natural alumina or synthetic alumina, e.g. highly porous alumina obtained by calcining α-alumina hydrate or β-alumina hydrate under appropriately controlled conditions. Some of commercially available activated alumina contain silica as the component for tablet-formation. The presence of silica in a content up to about 20% by weight to the total amount with alumina itself is practically not disadvantageous for production of the catalyst to be used in the process of the invention. When the amount is larger than about 50% by weight, the catalytic activity of the catalyst is extremely reduced to make the industrial use impossible.

As the fluorinating agent, there may be used an inorganic fluorinating agent or an organic fluorinating agent. Examples of the inorganic fluorinating agent are hydrogen fluoride, silicon tetrafluoride, sulfur fluoride (e.g. sulfur tetrafluoride, sulfur hexafluoride), sulfuryl fluoride, thionyl fluoride, ammonium fluoride (e.g. acidic ammonium fluoride, neutral ammonium fluoride), etc. Examples of the organic fluorinating agent include fluorohydrocarbons, chlorofluorohydrocarbons, bromofluorohydrocarbons, etc. Fluorine-containing compounds of the formula: $C_nF_aH_bX$ wherein X is an oxygen atom or a nitrogen atom, $n$ is an integer of 1 to 8 (preferably 1 to 4), $a$ is an integer of 1 to $2n + m$, $b$ is an integer of 0 to $2n + m - 1$ and $m$ is an integer of 2 when X is an oxygen atom or an integer of 3 when X is a nitrogen atom, as disclosed in Japanese Patent Publication (unexamined) No. 1578/1972, can be also used as the organic fluorinating agent. The fluorohydrocarbons may be saturated or unsaturated hydrocarbons having not more than 8, preferably not more than 4, carbon atoms in which at least one hydrogen atom is substituted with a fluorine atom. A higher degree of substitution with fluorine atoms is more preferable. Specific examples are $CF_4$, $CHF_3$, $CF_3CF_3$, $CHF_2CF_3$, $CHF_2CHF_2$, $CH_3CF_3$, $CH_2FCHF_2$, $CH_2=CF_2$, $CF_3CF=CF_2$, $CF_2=CF_2$, etc. The chlorofluorohydrocarbons and the bromofluorohydrocarbons may be saturated or unsaturated hydrocarbons having not more than 8, preferably not more than 4, carbon atoms in which hydrogen atoms are substituted with at least one fluorine atom and at least one chlorine or bromine atom and include specifically $CCl_3F$, $CCl_2F_2$, $CHCl_2F$, $CHClF_2$, $CClF_2CCl_2F$, $CCl_3CF_3$, $CCl_2FCCl_2F$, $CCl_3CCl_2F$, $CClF_2CClF_2$, $CCl_2FCF_3$, $CF_3CCl=CClCF_3$, $CF_2BrCFClBr$, $CF_2BrCHClF$, $CF_2BrCF_2Br$, etc. Examples of the fluorine-containing compounds are hexafluoroacetone, hexafluoro-1,2-epoxyethane, decafluorodiethyl ether, tri(trifluoromethyl)amine, tetrafluoroethyl methyl ether, etc. Among them, perfluoroalkanes such as tetrafluoromethane and perfluoroalkenes such as hexafluoropropene are particularly preferred.

The preparation of the catalyst may be carried out by various procedures depending on the kind of the fluorinating agent as employed.

When, for instance, hydrogen fluoride or ammonium fluoride is employed as the fluorinating agent, the activated alumina is contacted with it at a temperature of about 20° to 450° C so as to give the fluorinated alumina.

When sulfur fluoride, sulfuryl fluoride or thionyl fluoride is employed, the activated alumina may be contacted with the fluorinating agent at a temperature of about 300° to 500° C to give the fluorinated alumina. In some cases, sulfurous compounds may be formed and deposited on the catalyst, but they are not poisonous to the catalytic activity.

When the fluorinating agent is an organic fluorinating agent, the activated alumina may be contacted with it at a temperature of about 100° to 600° C, preferably of about 150° to 450° C to give the desired fluorinated alumina.

In case of using an organic fluorinating agent, the treatment of the activated alumina with a chlorohydrocarbon or a bromohydrocarbon may be effected prior to the contact with the organic fluorinating agent. The coexistence of a chlorohydrocarbon or a bromohydrocarbon on the contact of the activated alumina with the organic fluorinating agent is sometimes recommendable, since the fluorination of the activated alumina can be accomplished more smoothly under a lower temperature.

As the chlorohydrocarbon or the bromohydrocarbon, there may be employed a saturated or unsaturated hydrocarbon having not more than 8, preferably not more than 4, carbon atoms in which at least one hydrogen atom is substituted with a chlorine or bromine atom. A higher degree of substitution with chlorine or bromine atoms is more preferable. Substitution with chlorine or bromine atoms alone or with both of them is admissible. Specific examples are $CCl_4$, $CHCl_3$, $CCl_3CCl_3$, $CHCl_2CCl_3$, $CCl_2=CCl_2$, $CHCl=CCl_2$, $CHBr_3$, $CCl_2Br_2$, etc. Among them, perchlorohydrocarbons are particularly preferred.

Explaining the preparation of the fluorinated alumina by treatment of the activated alumina with the fluorohydrocarbon and the chlorohydrocarbon or the bromohydrocarbon, the activated alumina may be contacted first with the chlorohydrocarbon or the bromohydrocarbon at a temperature of about 100° to 400° C (preferably 100° to 200° C) and then with the fluorohydrocarbon at a temperature of about 100° to 400° C (preferably 100° to 350° C), whereby the fluorinated alumina can be obtained.

Alternatively, the activated alumina may be contacted with a mixture of the chlorohydrocarbon or the bromohydrocarbon and the fluorohydrocarbon at a temperature of about 100° to 400° C (preferably 200° to 300° C). The mixing proportion of the chlorohydrocarbon or the bromohydrocarbon to the fluorohydrocarbon is determined depending on their kinds. In the combination of tetrachloromethane and trichlorotrifluoroethane, for instance, the molar ratio of tetrachloromethane and trichlorotrifluoroethane is desired to be about 0.1 – 5 : 1.

In addition to the procedures as above, the fluorinated alumina may be produced by any conventional procedure, for instance, as described in Japanese Patent Publications Nos. 11605/1964 and 27748/1968.

When the catalyst is used for a long period of time, carbonaceous materials are deposited on its surface to lower the catalytic activity. In such case, the catalytic activity can be recovered by heating the catalyst in the presence of oxygen or an oxygen-containing material such as air at a temperature of about 350° to 500° C.

The process of the invention can be effected by contacting hexafluoropropene and oxygen with the fluorinated alumina as the catalyst in a per se conventional manner. Thus, hexafluoropropene and oxygen may be contacted with a fixed bed, moving bed or fluidized bed of the catalyst in an appropriate reaction vessel or tube in a continuous system or a closed system.

The mixing proportion of hexafluoropropene and oxygen is usually about 1 : 10 – 0.1 (molar ratio), preferably about 1 : 2 – 0.3. When the amount of oxygen is smaller than the lower limit of the said range, the conversion rate is low. When the amount of oxygen is larger than the upper limit, the efficiency of apparatus is reduced. In case of necessity, an inactive gas such as carbon dioxide, nitrogen or helium may be employed as the diluent.

The reaction temperature at the contact is usually from about 80° to 300° C, preferably from about 100° to 250° C. When the temperature is lower than the lower limit of the said range, the conversion rate is lowered. When the temperature is higher than the upper limit, the yield is reduced. At a temperature lower than about 80° C, the reaction hardly proceeds. At a temperature higher than about 300° C, the yield is extremely low. The reaction pressure may be an atmospheric pressure or a higher pressure. In general, a higher pressure is preferable for increasing the conversion rate and the yield. For industrial use, a pressure of about 0 to 20 $kg/cm^2G$ is usually adopted.

The contact time is determined on the other conditions, particularly temperature. At a higher temperature, a shorter contact time is adopted, and at a lower temperature, a longer contact time is desired, as in case of other usual reactions. In general, a contact time of 30 minutes or less (e.g. 0.5 second) is preferable. A longer contact time results in a higher conversion. From the economical viewpoint, a proper contact time may be chosen. For instance, a contact time of about 1 second to 10 minutes is usually adopted in a continuous system in which the temperature is about 100° to 250° C.

As already mentioned, the production of hexafluoropropanone-2 from hexaflouropropene has been hitherto effected by two steps of reaction. According to the process of this invention, the production can be effected more efficiently by only one step of reaction. On analyzing the reaction products, formation of 1,2-epoxyhexafluoropropane, which is the intermediate in the conventional process, is not confirmed. In the conventional process, the second step of reaction is usually carried out in the presence of a Lewis acid as the catalyst.

While the conventionally known oxidation catalyst (e.g. silica) for hexafluoropropene mainly produces 1,2-epoxyhexafluoropropane, it is revealed that the fluorinated alumina does not produce 1,2-epoxyhexafluoropropane. On the other hand, Lewis acids (e.g. alumina, aluminum trichloride) known as catalysts for rearrangement of 1,2-epoxyhexafluoropropane to hexafluoropropanone-2 do not exert any activity for the reaction of hexafluoropropene with oxygen. From these facts, the fluorinated alumina is presumed to result in the selective formation of hexafluoropropanone-2 in the oxidation of hexafluoropropene by its unexpected characteristics.

Practical and presently preferred embodiments of the invention are illustratively shown in the following Examples.

EXAMPLE 1

1. Preparation of catalyst:

In a reaction tube made of Pyrex glass (28 mm in diameter, 1000 mm in length) and vertically set up in an electric furnace, there is charged granular activated alumina having a particle size of 2.3 to 4.7 mm (alumina gel; "Neobead C-4" manufactured by Mizusawa Kagaku Co., Ltd.) (51.25 g). Dehydration is effected under heating at 500° C for 1 hour in nitrogen stream, and then the temperature is lowered to 200° C. The supply of nitrogen is stopped, and a mixed solution of $CCl_4$ and $CF_2ClCFCl_2$ (1 : 1 in molar ratio) is introduced at a rate of 1 g/min from the top of the reaction tube. The upper part of the alumina layer shows immediately a raise of the temperature up to 270° C. The zone of high temperature is gradually moved to the lower layer, and after 40 minutes, an equilibrium is attained whereby the whole alumina layer shows a temperature higher than the designed temperature by about 10° C. Then, the designed temperature is raised to 250° C. In this case too, there is caused a slight hot spot which moves to the lower layer with lapse of treating time and, after 45 minutes, passes the lowest layer. Further, the designed temperature is raised up to 300° C, whereby the raise of temperature is hardly shown. After the treatment for 40 minutes, the furnace is allowed to cool, and the catalyst is taken out. The thus obtained catalyst having a fluorine content of 9.9% by weight is designated as "catalyst I".

The preparation of the catalyst is effected in the same manner as mentioned above under the following conditions to obtain the catalysts designated as "catalyst II" and "catalyst III".

| Catalyst | $CCl_4/CF_2ClCFCl_2$ (molar ratio) | Velocity of current of mixed solution (g/min) | Treating time (hr) 200° C | 250° C | 300° C | Flourine content (% by weight) |
|---|---|---|---|---|---|---|
| II | 0.1 : 1 | 1.0 | 0.5 | 0.7 | 0.6 | 9.1 |
| III | 0 : 1 | 1.0 | 1 | 1 | 0.83 | 9.3 |

2. Preparation of hexafluoropropanone-2:

The catalyst I obtained in (1) (50 g) (apparent volume, 50 ml) is charged into a reaction tube made of Hastelloy C being 18 mm in inner diameter and 1 m in length. A mixture of hexafluoropropene and oxygen (1 : 0.7 in molar ratio) is introduced therein under the following conditions: temperature, 170° C; pressure, 5 kg/cm²G (gauge pressure); amount of supplied gas, 100 ml/min (25° C, 1 atmospheric pressure).

The produced gas discharged from the reaction tube at the time of 3 hours after the initiation of introduction of the gaseous mixture is subjected to gas chromatographic, infrared spectrographic and mass spectrographic analyses, whereby the following results are obtained:

| Compound | Mol % |
|---|---|
| $CF_3CF=CF_2$ | 65.6 |
| $CF_4$ | 7.3 |
| $CO_2$ | 1.5 |
| $COF_2$ | 6.6 |
| $CF_3COF$ | 3.1 |
| $CF_3COCF_3$ | 15.9 |
| $CF_3CFCF_2$ \\ /  $O$ | 0 |

EXAMPLES 2 TO 11 AND COMPARATIVE EXAMPLES 1 TO 5

Hexafluoropropene and oxygen are contacted with the catalyst in the same manner as in Example 1 (2) under the conditions shown in Table 1. The catalyst used is the same as prepared in Example 1 (1). The composition of the discharged gas at the time of 3 hours after the initiation of introduction of the gaseous mixture is examined by gas chromatographic, infrared spectrographic and mass spectrographic analyses. The results are shown in Table 1.

Table 1

| No. | | Reaction temperature (° C) | Reaction pressure (kg/cm²G) | HFP*/$O_2$* (molar ratio) | Total amount of flowing gas (ml/min)** | Material of reaction tube | Composition of Catalyst Kind | Amount (ml) | discharged gas (mol %) $CF_3CF=CF_2$ | $CF_4$ | $CO_2$ | $COF_2$ | $CF_3COF$ | $CF_3COCF_3$ | $CF_3CFCF_2$ \\ / $O$ |
|---|---|---|---|---|---|---|---|---|---|---|---|---|---|---|---|
| Example of invention | 2 | 215 | 0 | 1.4 | 120 | Pyrex glass | II | 50 | 66.6 | 12.3 | 2.0 | 6.0 | 0.4 | 12.3 | 0 |
| | 3 | 190 | 0 | 2.3 | 100 | Pyrex glass | II | 50 | 82.0 | 6.0 | 1.0 | 3.1 | 0.3 | 7.6 | 0 |
| | 4 | 220 | 0 | 0.8 | 260 | Pyrex glass | III | 50 | 80.1 | 9.3 | 1.5 | 4.6 | 0.5 | 4.0 | 0 |
| | 5 | 200 | 0 | 1.4 | 120 | Pyrex glass | I | 50 | 53.4 | 20.2 | 3.2 | 9.7 | 0.1 | 13.4 | 0 |
| | 6 | 250 | 0 | 1.0 | 140 | Pyrex glass | I | 50 | 51.5 | 22.5 | 3.3 | 9.9 | 0.5 | 10.3 | 0 |
| | 7 | 185 | 3.5 | 0.9 | 60 | Hastelloy C | II | 30 | 49.8 | 14.1 | 3.9 | 11.6 | 4.1 | 16.5 | 0 |
| | 8 | 145 | 3.4 | 0.9 | 40 | Hastelloy C | I | 30 | 58.5 | 9.3 | 2.7 | 8.2 | 3.3 | 18.0 | 0 |
| | 9 | 150 | 3.6 | 1.8 | 40 | Hastelloy C | III | 30 | 70.8 | 6.0 | 2.0 | 5.8 | 4.3 | 11.1 | 0 |
| | 10 | 170 | 4.5 | 1.8 | 60 | Hastelloy C | I | 30 | 65.9 | 7.2 | 2.0 | 6.0 | 3.0 | 15.9 | 0 |
| | 11 | 170 | 4.0 | 1.8 | 60 | Hastelloy C | I | 30 | 67.4 | 7.8 | 2.1 | 6.1 | 2.9 | 13.7 | 0 |
| Comparative Example | 1 | 270 | 0 | 1.0 | 100 | Pyrex glass | — | 0 | 40.2 | 0 | 7.7 | 23.2 | 23.2 | 0 | 5.7 |
| | 2 | 290 | 0 | 1.0 | 100 | Hastelloy C | — | 0 | 27.9 | 0 | 7.8 | 23.3 | 32.9 | 2.2 | 5.9 |
| | 3 | 200 | 0 | 1.4 | 1 120 | Pyrex glass | $Al_2O_3$ gel | 50 | 99.8 | 0 | 0.2 | 0 | 0 | 0 | 0 |
| | 4 | 200 | 0 | 1.4 | 120 | Pyrex glass | $AlF_3$ | 50 | No reaction occurs. | | | | | | |
| | 5 | 170 | 0 | 1.4 | 120 | Pyrex glass | $AlCl_3$ | 50 | | | | | | | |

Note:
*) HFP = Hexafluoropropene
**) 25° C, 1 atm.

EXAMPLE 12

In a 17 ml-volume autoclave made of stainless steel, the catalyst II obtained in Example 1 (1) (2.0 g) is charged, and the temperature is kept at 130° C. A mixture of hexafluoropropene and oxygen (1 : 1 in molar ratio) is introduced therein under pressure until the pressure becomes 5.0 kg/cm³. The composition of gas in the contents is examined by the gas chromatographic analysis 10 minutes and 1 hour after the initiation of the reaction. The results are shown in Table 2.

Table 2

| | Compositon of gas (mol %) | | | | | |
|---|---|---|---|---|---|---|
| | $CF_3CF=CF_2$ | $CF_4$ | $CO_2$ | $COF_2$ | $CF_3COF$ | $CF_3COCF_3$ |
| After 10 | 51.2 | 13.3 | 3.7 | 11.1 | 4.1 | 16.6 |

Table 2-continued

| | Compositon of gas (mol %) | | | | | |
|---|---|---|---|---|---|---|
| | $CF_3CF=CF_2$ | $CF_4$ | $CO_2$ | $COF_2$ | $CF_3COF$ | $CF_3COCF_3$ |
| minutes After 1 hour | 38.2 | 17.0 | 4.7 | 14.2 | 4.7 | 21.2 |

EXAMPLE 13

1. Preparation of catalyst:

A. In a reaction tube made of Pyrex glass (28 mm in diameter, 1000 mm in length) and vertically set up in an electric furance, there is charged granular activated alumina as used in Example 1 (1) (50 g). While introducing hexafluoropropene into the reaction tube, the temperature is elevated to 200° C, during which the generation of carbon monoxide and carbon dioxide is recognized at 160° C. The temperature is maintained at 200° C for 1 hour, during which hexafluoropropene is flowed in a rate of 80 ml/min (25° C, 1 atm.). Then, the temperature is elevated to 250° C, and this temperature is maintained for further 1 hour, during which hexafluoropropene is flowed in the same proportion as above. The temperature is further elevated up to 450° C in nitrogen stream and then oxygen is passed through in a rate of 100 ml/min (25° C, 1 atm.) for 1.5 hours. The thus obtained fluorinated alumina as the catalyst has a fluorine content of 4.02% by weight.

B. As in A, granular activated alumina (50 g) is charged in a reaction tube, and the temperature is elevated to 200° C in nitrogen stream. While maintaining this temperature, hexafluoropropene is flowed in a rate of 80 ml/min (25° C, 1 atm.) for 40 minutes. The temperature is elevated up to 450° C in nitrogen stream and then oxygen is passed through in a rate of 100 ml/min (25° C, 1 atm.) for 1.5 hours. The thus obtained fluorinated alumina has a fluorine content of 1.30% by weight.

C. As in A, granular activated alumina (50 g) is charged in a reaction tube, and the temperature is elevated to 350° - 370° C in nitrogen stream. While maintaining this temperature, sulfur hexafluoride is introduced into the reaction tube in a rate of 200 ml/min (25° C, 1 atm.) for a certain period of time as shown in Table 3, whereby the fluorinated alumina having a fluorine content as shown in Table 3 is obtained.

Table 3

| Fluorinated alumina No. | Time for treatment (hr) | Fluorine content (% by weight) |
|---|---|---|
| $C_1$ | 0.5 | 0.5 |
| $C_2$ | 1.8 | 2.5 |
| $C_3$ | 2.5 | 3.5 |
| $C_4$ | 5 | 5.5 |
| $C_5$ | 9 | 12.3 |

D. In a reaction tube made of Hastelloy C (18 mm in diameter, 1000 mm in length) and vertically set up in an electric furnace, there is charged granular activated alumina having a particle size of 2.3 to 4.7 mm ("Activated Alumina KH-A46" manufactured by Sumitomo Chemical Company, Limited) (50 g). The temperature is elevated to 120° C in nitrogen stream, and then hydrogen fluoride is flowed in a rate of 100 ml/min (25° C, 1 atm.) at 120° C for 4 hours. Then, the temperature is elevated up to 420° C in nitrogen stream, and this temperature is maintained for 3 hours for elimination of water and hydrogen fluoride, whereby the fluorinated alumina having a fluorine content of 30% by weight is obtained.

E. In a 200 ml volume autoclave made of stainless steel, granular activated alumina having a particle size of 2.3 to 4.7 mm (alumina gel; "Neobead C-4" manufactured by Mizusawa Kagaku) (50 g) is charged, and the atmosphere is reduced to vacuo. Hydrogen fluoride (1 g) is introduced into the autoclave, whereby the generation of heat is observed. After 40 minutes, the temperature is heated at 100° C for 1 hour and then elevated to 420° C. The contents are maintained at this temperature under a pressure of 0.1 mmHg for 3 hours, whereby water and hydrogen fluoride are eliminated. The thus obtained fluorinated alumina has a fluorine content of 2.63% by weight.

F. As in (D), granular activated alumina is treated with gaseous hydrogen fluoride in a rate of 200 ml/min (25° C, 1 atm.) at 140° C for 4 hours, whereby the fluorinated alumina having a fluorine content of 49.8% by weight is obtained.

G. Granular activated alumina as in D (50 g) is immersed in a 20% aqueous solution of ammonium fluoride for 30 minutes. The activated alumina is taken out from the ammonium fluoride solution, dried at room temperature under reduced pressure and then charged in a reaction tube made of Hastelloy C. The reaction tube is heated at 550° C for 5 hours, during which nitrogen is passed through. The obtained fluorinated alumina has a fluorine content of 4.5% by weight.

H. As in (D), granular activated alumina (40 g) is treated with sulfuryl fluoride (300 ml/hour, at 25° C, 1 atm.) at 427° C for 3 hours, whereby the fluorinated alumina having a fluorine content of 1.5% by weight is obtained.

2. Preparation of hexafluoropropanone-2:

The catalyst obtained in (1) (40 g) is charged into a reaction tube made of Hastelloy C being 18 mm in inner diameter and 1 m in length. A mixture of hexafluoropropene and oxygen (1 : 1 in molar ratio) in introduced therein under the following conditions: temperature, 175° C; pressure, 1 atm.; amount of supplied gas, 80 ml/min (25° C, 1 atm.). The composition of the discharged gas is examined by gas chromatographic analysis. The results are shown in Table 4.

Table 4

| Fluorinated alumina No.[*)] | Fluorine content in catalyst (% by weight) | | Compositions of discharged gas (mol %) | | | | | |
|---|---|---|---|---|---|---|---|---|
| | Initial | After 50 hours | $CF_4$ | $CO_2$ | $COF_2$ | $CF_3COF$ | $CF_3CF=CF_2$ | $CF_3COCF_3$ |
| H | 1.50 | 8.22 | 5.0 | 1.5 | 4.4 | 3.0 | 74.2 | 11.9 |
| $C_2$ | 2.50 | 8.13 | 5.3 | 1.5 | 4.2 | 3.0 | 73.7 | 12.3 |
| E | 2.63 | 8.20 | 5.2 | 1.7 | 4.0 | 3.0 | 74.4 | 11.7 |
| G | 4.50 | 7.90 | 4.4 | 2.8 | 4.5 | 3.5 | 72.8 | 12.0 |
| A | 4.02 | 8.12 | 5.2 | 1.8 | 4.2 | 3.8 | 72.7 | 12.3 |

Table 4-continued

| Fluorinated alumina No.*) | Fluorine content in catalyst (% by weight) | | Compositions of discharged gas (mol %) | | | | | |
| --- | --- | --- | --- | --- | --- | --- | --- | --- |
| | Initial | After 50 hours | CF$_4$ | CO$_2$ | COF$_2$ | CF$_3$COF | CF$_3$CF=CF$_2$ | CF$_3$COCF$_3$ |
| C$_5$ | 12.3 | 12.4 | 5.5 | 1.0 | 3.8 | 3.8 | 73.4 | 12.5 |
| D | 30.0 | 30.0 | 2.1 | 0.4 | 2.6 | 2.5 | 87.6 | 4.8 |
| F | 49.8 | 49.8 | 0.5 | 0.1 | 0.3 | 0.1 | 98.2 | 0.8 |

Note:
*)Corresponding to the procedure as above.

EXAMPLE 14

1. Preparation of catalyst:

In a reaction tube made of Hastelloy C (18 mm in inner diameter, 1000 mm in length) and vertically set up in an electric furnace, there is charged granular activated alumina as used in Example 1 (1) (50 g). Dehydration is effected at 450° C for 2 hours in nitrogen stream, and then the temperature is lowered to 170° C. The supply of nitrogen is stopped, and a mixture of $C_2F_6$ and $O_2$ (1 : 1 in molar ratio) in introduced at a rate of 80 ml/min (25° C, 1 atm.) from the top of the reaction tube. The temperature of the alumina layer shows a temporary elevation and, after 30 minutes, indicates the recovery to 170° C. At this temperature, the introduction of the said mixture is continued for 1.5 hours, during which the production of $CO_2$ in trace is detected. Then, the temperature is raised to 200° C, and the introduction of the mixture is continued for 4 hours, during which the formation of a small amount of $CO_2$ is confirmed. Thereafter, the inner temperature rises gradually, and the production of $CF_3COCF_3$ and $CF_4$ is detected with the increase of the produced amount of $CO_2$, at which the inner temperature reaches to 220° C in 2 hours. The reaction tube is allowed to cool by passing nitrogen through the same, and the catalyst is taken out. The fluorine content of the thus obtained catalyst is 1.8% by weight. Deposition of carbonaceous materials is not recognized.

2. Preparation of hexafluoropropanone-2:

The catalyst obtained in (1) (40 g) is charged into a reaction tube made of Hastelloy C being 18 mm in inner diameter and 1 m in length, and the temperature is elevated to 160° C. Hexafluoropropene and oxygen are introduced into the reaction tube at amounts of 30 ml/min and of 20 ml/min (25° C, 1 atm.) respectively, whereby the inner temperature is rapidly elevated to 190° C and an equilibrium is attained at this temperature. The composition of the gaseous mixture taken out from the reaction tube at this time is as follows: CF$_4$, 1.2 mol%; CO$_2$, 10.5 mol%; CF$_3$COCF$_3$, 2.1 mol%; C$_3$F$_6$, 86.2 mol%. Then, the inner temperature is gradually lowered and reaches to a constant temperature of 177° C about 15 hours after the initiation of introduction of hexafluoropropene and oxygen. At this time, the gaseous mixture from the reaction tube shows the following composition: CF$_4$, 4.8 mol% CO$_2$, 1.1 mol%; COF$_2$, 3.8 mol%; CF$_3$COF, 1.2 mol%; CF$_3$COCF$_3$, 13.3 mol%; C$_3$F$_6$, 75.8 mol%. The supply of hexafluoropropene and oxygen is further continued until the elapse of about 30 hours from the initiation, during which the proportion of CF$_4$, COF$_2$ and CF$_3$COCF$_3$ is a little increased with an tendency of the decrease of CO$_2$ and CF$_3$COF. The fluorine content of the catalyst taken out from the reaction tube after the finish of the reaction is 8.30% by weight.

EXAMPLE 15

In a reaction tube made of Hastelloy C, the catalyst C$_4$(40 g) is charged, and the temperature is elevated to 150° C in nitrogen stream. Then, C$_3$F$_6$ and O$_2$ are introduced into the reaction tube respectively in amounts of 40 ml/min and of 20 ml/min (25° C, 1 atm.) under a gauge pressure of 3 kg/cm$^2$G. After 20 hours, the gaseous mixture taken out from the reaction tube has the following composition: CO, 0.5 mol%; CF$_4$, 1.5 mol%; CO$_2$, 1.0 mol%; COF$_2$, 12.0 mol%; CF$_3$COF, 12.3 mol%; CF$_3$COCF$_3$, 26.2 mol%; C$_3$F$_6$, 46.5 mol%.

What is claimed is:

1. A process for preparing hexafluoropropanone-2 from hexafluoropropene which comprises contacting at a temperature of 80° to 300° C. hexafluoropropene and oxygen in a molar ratio of 1:10–0.1 with a fluorinated alumina containing fluorine in a concentration of 0.5 to 50% by weight.

2. The process according to claim 1, wherein the fluorinated alumina is the one prepared by reacting activated alumina with a fluorinating agent.

* * * * *